United States Patent [19]

Alexander

[11] Patent Number: 4,876,358
[45] Date of Patent: Oct. 24, 1989

[54] OXYETHYLENE BISMALEIMIDE DERIVATIVES

[75] Inventor: David C. Alexander, Austin, Tex.

[73] Assignee: Texaco Inc., White Plains, N.Y.

[21] Appl. No.: 125,086

[22] Filed: Nov. 25, 1987

[51] Int. Cl.$^4$ .................................. C07D 207/452
[52] U.S. Cl. .................... 548/521; 548/522; 526/262
[58] Field of Search .................. 548/521, 522

[56] References Cited

U.S. PATENT DOCUMENTS

| | | | |
|---|---|---|---|
| 3,766,138 | 10/1973 | Crivello | 528/170 |
| 3,855,239 | 12/1974 | Crivello | 548/521 |
| 3,951,902 | 4/1976 | Jones | 524/430 |

OTHER PUBLICATIONS

White (I), White, "Reactions of Diaminoalkanes . . . ", 1984, J. of Appl. Polymer Sci, vol. 29, 891–899.
White (II), White, "Synthesis & Properties of High Mol Wt Step-Gr . . . ", 1986, Ind Eng. Chem. Prod. Res. Dev., vol, 25, 395–400.

*Primary Examiner*—Mukund J. Shah
*Assistant Examiner*—Frederick F. Tsung
*Attorney, Agent, or Firm*—Jack H. Park; Kenneth R. Priem; Cynthia L. Kendrick

[57] ABSTRACT

Novel bismaleimides of the formula

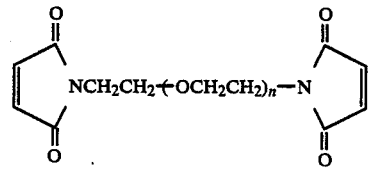

wherein n=1, 2, or 3 are formed in two steps by reacting a diamine and maleic anhydride to form a bismaleamic acid which is reacted with acetic anhydride in the presence of acetone to form the bismaleimide.

The bismaleimide monomer and prepolymers and the polybismaleimides formed from them may have improved flexibility, processibility, toughness and solubility.

1 Claim, No Drawings

OXYETHYLENE BISMALEIMIDE DERIVATIVES

BACKGROUND OF THE INVENTION

1. Technical Field of the Invention

This invention relates to bismaleimides. More particularly, this invention relates to novel bismaleimide derivatives obtained from oxyethylene diamines and anhydrides. Still more particularly, this invention relates to novel bismaleimide derivatives prepared by reacting at least about 0.5 mole equivalents of di-, tri- or tetraethylene glycol diamines with maleic anhydride in a two-step process.

The bismaleimide monomers and prepolymers formed have improved solubility and processibility; the polymers they are used to prepare may be tougher and more flexible than other polybismaleimides.

They may be used alone as monomers to give homopolymers, or in combination with other materials such as aliphatic or aromatic diamines or unsaturated compounds including aromatic bismaleimides to give copolymers.

2. Prior Art

Bismaleimide polymers are important primarily for their thermal stability, which usually results from aromaticity in the structure. Although the majority of bismaleimides have therefore prepared from aromatic diamines, aliphatic compounds can also provide benefits in improved processibility, flexibility and solubility, Bismaleimides have, for example, been prepared from alkylene-diamines (J. Appl. Poly. Sci, 29, 891–899 (1984) and from JEFFAMINE® ED-diamines (U.S. Pat. No. 3,951,502). In a series of Japanese patents issued to Mitsui Toatsu Chemicals (JP 82 205,413; 83 40,374; 83 15,515; 83 136,637), bismaleimides were also prepared from diamines such as 4,7-dioxadecane-1,10diamine (reduction product of cyanoethylated ethylene glycol) and related diamines; these are used with polybutadiene in preparation of copolymers. The maleimide of triethylene glycol monoamine is also reported in one of these patents. Use of the oxyethylene group to increase flexibility has been effective in some other types of polymers as well. In J. Macromol. Sci.—Chem., A21, 1117–1135 (1984) there is described preparation of "reactive plasticizers" with acetylene end-groups and internal oxyethylene groups. Stenzenberger, in German Pat. No. 2,127,024 disclosed the preparation of an aliphatic bismaleimide from 2,2,4-trimethylhexane-1,6-diamine and in German Pat. No. 2,165,974 he described its thermal polymerization.

The use of mixtures of polyoxyalkylene bismaleimides (with molecular weights greater than 400) and aromatic bismaleimides in preparation of flexibilized polybismaleimides is disclosed by de Koning in European patent application No. 206,383. While the heat distortion temperature fell with increasing amounts of flexibilizing bismaleimide, the elongation and flexure at break both increased.

In U.S. Pat. No. 4,237,262, Jones discloses a low temperature curable composition comprising at least one curable polyimide prepolymer formed by heating an aliphatic oxyalkylene bismaleimide with an aromatic polyamine and at least one aromatic bismaleimide and at least one aliphatic epoxy resin. The reaction product provides at least two functional epoxy groups to provide a low temperature curable composition. In U.S. Pat. No. 3,951,902 Jones et al. discloses a compliant polyimide having superior thermal mechanical properties produced by reacting an aromatic bis(furfurylimide) with an aliphatic ether bis(maleimide) via a Diels-Alder reaction.

In U.S. Pat. No. 4,116,937, Jones also discloses a resin system prepared by Michael addition of a mixture of oxyalkylene and aromatic bismaleimides to aromatic diamines. The oxyalkylene bismaleimides have molecular weights of about 750, and the product is a glassy solid at room temperature.

In the work described in 4,116,937 the objective was to make elastomers. The elongations for the polymers described in the examples therein range from 70% to 170%. These polymers were probably not very rigid, this property being a function of the molecular weight of the amines used and the distance between maleimide units. Another disadvantage is that the amines used here are aromatic amines, which are in many cases known or suspected to be carcinogenic or otherwise toxic; although the tissue is not specifically addressed, it is not likely the "flexible polyimide precursor", with its aromatic content, would be soluble to any great extent in water.

Nagaski, in European patent application No. 191,931, reveals the use of certain oxyalkylene bismaleimides in rubber compositions.

A curable resin composition is disclosed in Jpn. Kokai Tokkyo Koho JP 58, 136,637 [83,136,637] 13 Aug. 1983 to Mitsui Toatsu Chemicals. The compound contains an aliphatic imide and polybutadiene containing double bonds.

A Japanese Patent to Mitsui Toatsu Chemicals, Inc. (JP 58,127,735 [83,127,735] (Cl. C08G 73/10), 29 July 1983) discloses heat resistant electrical insulators for printed circuit boards which are prepared from mixtures of aliphatic polyether bisimides, aromatic bisimides and diamines.

An aritcle by White in *Ind. Eng. Chem. Prod. Res. Dev.* 25, 395–400 discusses the fact that bisimides offer potential for the synthesis of high-molecular-weight, step growth polymers. It is stated they are flanked by two electron-withdrawing carbonyl groups, and the electrophilic maleimide carbon-carbon-double bond is especially labile to nucleophilic attack and yields Michael type adducts with both amines and thiols. The paper focuses on the requirements for preparation of these polymeric Michael adducts, with additional emphasis on the effects of the enormous structural variety available within the class in thermal and physical properties of these new resins.

In the art experimental data are available wherein polymers were synthesized which are structurally related to those formed by nucleophilic or Michael addition of diaminoarenes, but which had more flexible backbones and lower glass transition temperature (Tg). See "Reaction of Diaminoalkanes with Bismaleimides: Synthesis of Some Unusual Polyimides", *Journal of Applied Polymer Science*, Vol. 29, 891–899 (1984).

Shaw and Kinloch have studied the effects of rubber concentration on the morphology, bulk mechanical and thermal properties and the adhesive strength of the bismaleimide by the addition of various amounts of a carbonyl-terminated butadiene (CTBN) rubber toughening agent, and concluded that surprisingly large amounts of CTBN rubber can be added to substantially improve the fracture resistance of the bismaleimide resin without sacrificing other important properties.

(See "Toughened Bismaleimide Adhesives", *Int. J. Adhesion*, July 1985, pp. 123-127.)

A growing number of applications for polyimides are discussed in the an article titled "Premium Performance from Polyimides" in ME, January 1986, p. 14–19.

In U.S. Pat. No. 4,277,582 Mueller discloses water-insoluble hydrophilic copolymers consisting of a hydrophilic polymer of monoolefinic monomers cross-linked with a major amount of a diolefinic non-hydrophilic macromer.

It appears there is a large market for bismaleimides and a good deal of research in the art has been directed toward studying properties of and better methods for producing these compounds. Bismaleimide compounds are increasingly important in high performance polymers commonly used as matrix resins for composites. It is believed that polybismaleimide derivatives of the instant invention, particularly those derived from di-, tri- and tetraethylene glycol diamines including bisaminoethyl ether, JEFFAMINE ® EDR-148 and JEFFAMINE ® EDR-192 would be useful as monomers in homopolymers and copolymers and would exhibit advantages including improved flexibility, processibility, toughness and solubility. They could be used alone or in combination with other materials such as aliphatic or aromatic diamines or unsaturated compounds (including aromatic bismaleimides) to give copolymers.

The series of oxyethylene diamines consisting of BAEE (bisaminoethyl ether, or diethylene glycol diamine), JEFFAMINE ® EDR-148 (triethylene glycol diamine), and JEFFAMINE ® EDR-192 (tetraethylene glycol diamine) are promising candidates for conversion to bismaleimides (eqs. 1,2). Incorporation of bismaleimides made from these diamines could give new prepolymers and polymers with enhanced flexibility, processibility of solubility. The polymer prepared from the adduct of EDR-148 and EDR-148 BMI was a relatively hard material with a high flexural modulus (close to 500,000 psi). In the instant invention there was less distance between the maleimide units than in, for example, the case of 4,116,937, where the amines had a minimum molecular weight of 600, and therefore the instant polymers exhibited more rigidity. Another advantage of the instant invention is that the prepolymer products exhibit solubility in water unlike products resulting from the use of aromatic amines.

One derivative, in particular, is the bismaleimide of triethylene glycol diamine. This bismaleimide should be quite useful as a monomer, but it is solid. This detracts from its usefulness for many applications. By a method disclosed in a second embodiment of the instant invention it is converted to a liquid form suitable for polymerization. Water-soluble bismaleimides and polybismaleimides have been sought in recent years, and compounds such as the prepolymers of this invention could prove to be especially useful in this respect.

SUMMARY OF THE INVENTION

In accordance with the present invention, bismaleimide and polybismaleimide derivatives are prepared from di-, tri-, and tetraethylene glycol diamines in a two-step process from the diamines and maleic anhydride according to equatins 1 and 2:

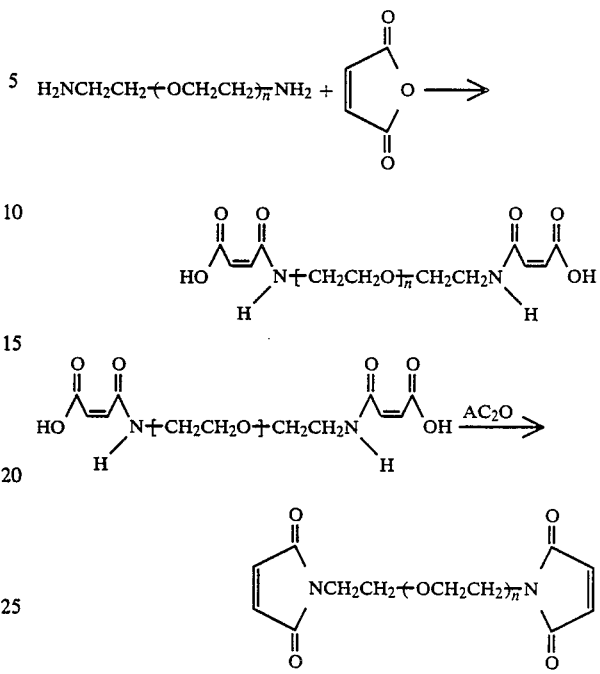

The potential for improved flexibility, processibility, toughness, and solubility make these compounds useful as monomers, or to provide prepolymers or homopolymers, or in combination with other materials such as aliphatic or aromatic diamines, or unsaturated compounds (including aromatic bismaleimides) to provide copolymers.

DETAILED DESCRIPTION

The oxyethylene bismaleimides of the present invention are prepared from an oxyethylene diamine having the formula:

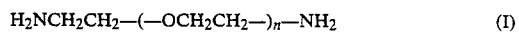

$$H_2NCH_2CH_2-(-OCH_2CH_2-)_n-NH_2 \quad (I)$$

where n=2, 3 or 4 which is combined with maleic anhydride of the formula:

to form a bismaleamic acid of the formula:

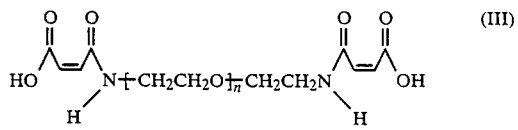

which is reacted with acetic anhydride in the presence of acetone solution to form a bismaleimide of the formula:

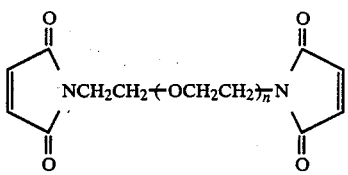

(IV)

where n=2, 3 or 4.

Diamine Starting Materials

The oxyethylene diamine reactants represented by (I) above include di-, tri-, and tetraethylene glycol diamine compounds.

Of special note are the "JEFFAMINE ® EDR series diamines". The structure of "JEFFAMINE ® EDR" can be generically illustrated as follows:

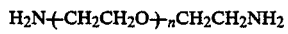

where n=2,3.

In one example the diamine used is JEFFAMINE ® EDR-148. JEFFAMINE ® EDR-148 is the trademark for a triethylene glycol diamine produced by Texaco Inc. In another example the diamine is JEFFAMINE ® EDR-192. JEFFAMINE ® EDR-192 is the trademark for tetraethylene glycol diamine produced by Texaco.

Preparation of the bismaleimides is effected by reacting a diamine with 2 moles of maleic anhydride. These reactants are mixed with a small amount of solvent to facilitate the mixing process and the solvent is subsequently driven off after the bismaleimide is formed.

Preparation of the Bismaleimides

It has been discovered in accordance with the present invention that a bismaleimide product is preferentially formed when a bis(amic acid) (prepared from the oxyethylene diamines and maleic anhydride) is reacted with an excess of anhydride at autogenous pressure at a temperature within the range of about 50° to about 150° C. for a reaction time within the range of about 0.5 to about 12 hours. Good results are obtained heating the mixture at 60° to 100° for 0.5 to 4 hours to provide complete reaction of the diamine and the anhydride. Normally, the reaction will go to completion after a reaction time within the range of about 1-2 hours.

The reaction is complete when essentially all of the diamine has reacted with maleic anhydride. Under the noncatalytic reaction conditions employed herein, the amine groups of the polyoxyalkylene diamines are essentially unreactive with each other.

The bismaleimide monomers and prepolymers that are formed by the process of the present invention are liquid or crystalline solid materials having a molecular weight within the range of about 250 to about 1000 and containing no terminal primary amine groups.

The reaction mixture will comprise a diamine addition product which may be generally characterized by the following formula:

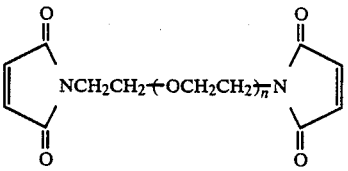

wherein n represents 2, 3 or 4.

A variety of molecular configurations is possible for the bismaleimides of the present invention, depending on the starting materials. For example, where the starting materials is bisaminoethyl ether and maleic anhydride, the bismaleimide will have the formula:

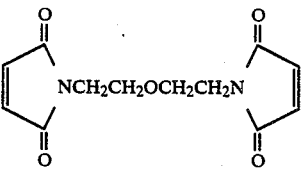

Where the diamine is JEFFAMINE ® EDR-148 and the anhydride is maleic anhydride, the reaction product will be composed principally of a bismaleimide having the formula:

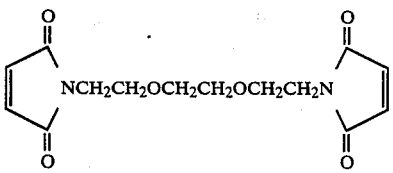

Where JEFFAMINE ® EDR-192 is reacted with maleic anhydride, the reaction product that is formed will be composed principally of a bismaleimide addition product having the formula:

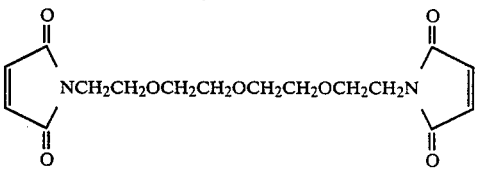

In another embodiment of this invention the solid bismaleimides of this invention are converted to liquid prepolymers.

The significance of this invention is that the bismaleimide of triethylene glycol diamine or other solid oxyethylene bismaleimide should be quite useful as a monomer except that it is a solid, which detracts from its utility for many applications. By conversion into the prepolymer the oxyethylene bismaleimide is unexpectedly converted into a liquid form suitable for polymerization. The liquid products can be cured thermally to give hard polymers. The polymers are potentially useful as matrix resins or components thereof containing ether linkages that may impart improved processibility.

The liquid form is obtained from the bismaleimide by reacting the solid with EDR-148 to give a liquid bismaleimidoaspartimide prepolymer. In many applications liquids are preferable to solids and the liquid prepolymers can be cured thermally.

This can be represented by equation 3:

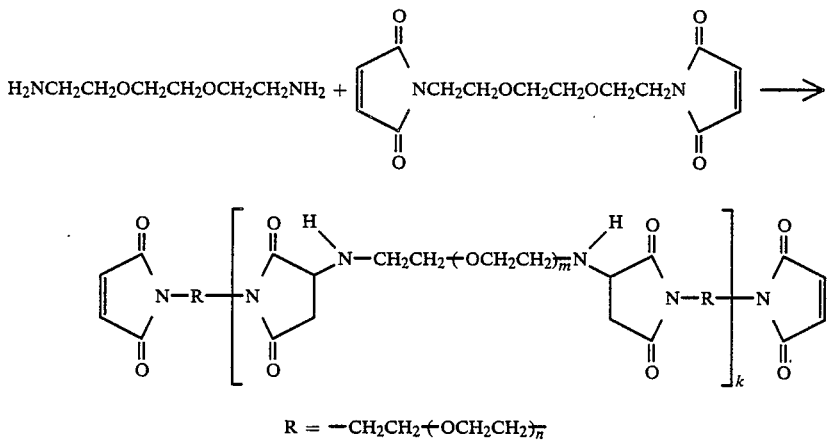

where m=2, n=2 and k is predominantly 1.

Of course, other examples of such prepolymers can be prepared from other oxyethylene diamines and their BMI derivatives.

The preparation of the prepolymer is carried out at temperatures up to 125° and polymerization is carried out at subatmospheric or superatmospheric pressures.

In Examples I through VI the preparation of three bismaleiamic acids were quite similar and were based on the preparations of bismaleimides from alkylene-diamines reported by White (J. Appl. Poly. Sci. 29, 891–899 (1984), incorporated herein by reference.

Example VII demonstrates the preparation of the bismaleimidoaspartimide.

Example VIII demonstrates the use of the bismaleimidoaspartimide in polymer preparation.

The following examples are given in the way of illustration only and are not intended as limitations on the scope of the invention.

EXAMPLE I

In the preparation of the bismaleimic acid from triethylene glycol diamine, maleic anhydride (62 g, 630 mmol) was dissolved in 250 ml chloroform; the solution was cooled to 8° C. in a 500 ml 3-necked round-bottom flask equipped with mangetic stirrer and nitrogen inlet. Triethylene glycol diamine (48 g, 320 mmol) was added dropwise (with the temperature kept below about 10° C.) over a period of three hours, which led to precipitation of a white solid within the first hour. After the addition was complete, the slurry was allowed to warm to room temperature and stirred for two hours more. The mixture was then filtered; after it was dried under vacuum a white powder (150 g, 95%) was obtained, m.p. 150–151.5. Titration of this solid showed an acid content of 5.77 meq/g; theoretical acid content is 5.78 meq/g. Spectra (nmr, ir) were consistent with the assigned structure.

EXAMPLE II

Preparation of the tetraethylene glycol diamine maleamic acid was carried out similarly, but this material did not precipitate as a solid. Near the end of the addition two phases appeared; the upper phase was a chloroform solution of the bismaleimic acid. After removal of the chloroform the residual oil solidified and gave, after drying under vacuum, a white powder (53 g, 87%), m.p. 96°–101° C. Titration of this solid gave an acid content of 5.24 meq/g; theoretical acid content is 5.15 meq/g. Spectra (nmr, ir) were consistent with the assigned structure.

EXAMPLE III

The bismaleamic acid from diethylene glycol diamine precipitated immediately on addition of the amine to the anhydride solution and was isolated as a white powder. After it was dried under vacuum 60.3 g (96%) was obtained, m.p. 164°–166° C. The acid content was found by titration to be 6.73 meq/g; the theoretical acid content is 6.67 meq/g. Spectra (nmr, ir) were constent with the assigned structure.

EXAMPLES IV-VI

Examples IV through VI represent the second step of the two-step process wherein the bismaleimides are prepared from the bismaleimic acids.

The bismaleimides were prepared by reaction of the bismaleamic acid with acetic anhydride in acetone solution in the presence of triethylamine and acetate salts.

EXAMPLE IV

In the preparation of triethylene glycol diamine bismaleimide, the bismaleamic acid (60 g, 0.17 mol), triethylamine (11.5 g, 0.11 mol), and sodium acetate trihydrate (1.9 g, 0.13 mol) were added to acetone (200 ml) in a 1000 ml 3-necked round bottomed flask fitted with nitrogen inlet and magnetic stirrer. Acetic anhydride (110 g, 1.08 mol) was added, and the resulting mixture was heated at reflux (70°) for 2.5 hours; during this period the solid dissolved and the solution darkened. About 60 ml acetone were then distilled. The residue was allowed to cool to 50°, and most of the rest of the acetone was removed under vacuum with the temperature kept below 60°. Some solid appeared in the dark residue, and the resulting paste was poured into 500 ml stirred distilled water. A precipitate formed and was filtered from the dark solution, then washed on the filter with methanol (3×40 ml) and dried under vacuum to give 20 g (37%) off-white powder, m.p. 92°–93°. Spectra (nmr, ir) were consistent with the assigned structure.

EXAMPLE V

When tetraethylene glycol diamine (JEFFAMINE ® EDR-192) was the bismaleimic acid precursor, a solid bismaleimide could not be prepared. Instead, a dark, viscous liquid formed which was more soluble than the other two products and could not be induced to solidify. The proton nmr spectrum of this material appeared to be that of a mixture containing a major amount (ca. 70% by nmr) of the desired bismaleimide along with smaller portions of unidentified impurities.

EXAMPLE VI

Preparation of the bismaleimide from diethylene glycol diamine was carried out identically and afforded a very light tan solid, m.p. 154.5°–156.5°. Spectra (nmr, ir) were consistent with the assigned structure.

Heating of these bismaleimides alone at 180°–200° for 0.5–1.0 hours gave hard, transparent, somewhat brittle brown polymers with decomposition temperatures found by thermogravimetric analysis to be approximately 440° C. (bisaminoethyl ether derivative) and 4003 C. (triethylene glycol diamine derivative).

EXAMPLE VII

Example VII demonstrates the preparation of the bismaleimidoaspartimide from the triethylene glycol bismaleimide. In a 250 ml 3-necked round-bottomed flask, under nitrogen, a solution of triethylene glycol diamine (1.68 g, 11.3 mmol) in 10 ml chloroform is added dropwise to a solution of triethylene glycol bismaleimide (7.00 g, 22.7 mmol) in 40 ml chloroform at 40°. The resulting orange solution is heated at reflux for 1.5 hours and then concentrated under vacuum to give approximately 8.1 g of the prepolymer as a viscous orange liquid.

EXAMPLE VIII

Example VIII demonstrates the use of the bismaleimidoaspartimide in polymer preparation. A 17.5 g sample of the prepolymer was heated at 60° under vacuum for 3 hours, then poured into a 5"×3.25" mold which was placed into an oven at 125°. The oven was heated to 165° over a one hour period and then held at 165°–175° for an additional two hours. The product polymer was obtained as a hard, red, fairly stiff plaque with a room temperature flexural modulus (ASTM D-790) of 46,000 psi.

What is claimed is:

1. A liquid bismaleimidoaspartimide prepolymer comprising 60 to 90 weight percent bismaleimide of the formula:

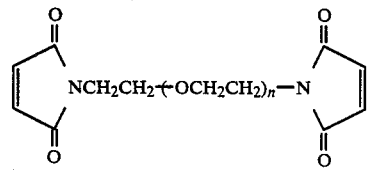

wherein $n=2$ and 10 to 40 weight percent triethylene glycol diamine.